United States Patent
Percino Zacarias et al.

(10) Patent No.: US 7,989,583 B2
(45) Date of Patent: Aug. 2, 2011

(54) PROCESS TO OBTAIN DIMERS, TRIMERS AND UP TO POLYMERS FROM PYRIDINMETHANOL DERIVATIVES COMPOUNDS

(75) Inventors: Maria Judith Percino Zacarias, Cholula (MX); Victor Manuel Chapela Castanares, Cholula (MX); Berenice Herrera De La Luz, Puebla (MX)

(73) Assignee: Benemerita Universidad Autonoma de Puebla, Puebla (MX)

( * ) Notice: Subject to any disclaimer, the term of this patent is extended or adjusted under 35 U.S.C. 154(b) by 0 days.

(21) Appl. No.: 12/183,167

(22) Filed: Jul. 31, 2008

(65) Prior Publication Data
US 2009/0043063 A1 Feb. 12, 2009

(30) Foreign Application Priority Data
Aug. 1, 2007 (MX) .................. MX/A/2007/009292

(51) Int. Cl.
C08G 61/00 (2006.01)
C08G 61/12 (2006.01)
C08G 73/00 (2006.01)
C08G 73/06 (2006.01)

(52) U.S. Cl. ............ 528/423; 526/263; 546/26; 546/27; 546/255

(58) Field of Classification Search .................. 526/263; 546/255
See application file for complete search history.

(56) References Cited

OTHER PUBLICATIONS

Percino et al. "Synthesis, characterisation and crystal structure of 1,2-bis(6-methylpyridin-2-yl)ethene-1,2-diol". J. Chem. Res. 2005, 12, 757-760.*

Alan R. Katritzky, Andrzej R. Lapucha, and Michael Siskin. "Aqueous high-temperature chemistry of carbo and heterocycles. 3. 2-Substituted pyridines" Energy & Fuels 1990, 4(5), 506-510.*

Percino et al. "Synthesis, Characterisation and Crystal Structure of a co-crystal of two components: 1,2-bis(6-methylpyridin-2-yl)ethane-1,2-dione and 1-(pyriin-2-yl)-2-(6-methylpyridin-2-yl)ethane-1,2-dione". J. Chem. Res. 2007, 3, 185-189.*

Robert B. Moll, Edward J. Poziomek, and William A. Mosher. "Chemistry of di-2-pyridylglyoxal". J. Org. Chem. 1971, 36(8), 1056-1061.*

Percino et al. "Synthesis of 1,2-dimethoxy-1,2-di(pyridin-2-yl)1,2-ethanediol: Crystal and molecular structure determination". J. Chem. Cryst. 2006, 36(5), 303-308.*

* cited by examiner

*Primary Examiner* — Vasu Jagannathan
*Assistant Examiner* — Richard A Huhn
(74) *Attorney, Agent, or Firm* — Roylance, Abrams, Berdo & Goodman, L.L.P.

(57) ABSTRACT

The dimerization or polymerization reaction of pyridinic alcohols is carried out in order to produce novel products. The process is carried out in the absence or presence of some solvent, during the process of the current invention, temperature may be or may be not used as catalyst, in the process of the current invention the reaction may be or may not be catalyzed by the presence of a catalyst (acid or base), the resultant products can be produced and separated in an easy way, in the process of the current invention starting from pyridinic alcohols the resultant ethenediols can be produced by a single step reaction. The pyridinemethanol derivatives used as starting compounds, do not oxidize as easily and their handling is easier than that of other compounds. The products produced with etheneidol parts can be used as antioxidants due to their capacity to act as free radicals scavengers.

5 Claims, 4 Drawing Sheets

PROCESS TO OBTAIN DIMERS, TRIMERS AND UP TO POLYMERS FROM PYRIDINMETHANOL DERIVATIVES COMPOUNDS

CROSS-REFERENCE TO RELATED APPLICATION

This application claims the benefit of Mexican Patent Application No. MX/a/2007/009292, filed Aug. 1, 2007, the disclosure of which is hereby incorporated by reference in its entirety.

FIELD OF THE INVENTION

The current invention is referred to the field of certain ethenediol products, as well as to the process to obtain them from pyridine derivatives compounds, it was possible to obtain these products as dimers, trimers up to polymers, which show characteristics as antioxidants due to their ability to inhibit free radicals.

BACKGROUND OF THE INVENTION

Benzoin type condensation is of interest, among other aspects, to: 1) in biochemistry as a model to form carbon-carbon bonds, 2) it is the classical example of specific catalysis, 3) the benzoin condensation shown in reaction 1 below is of organic chemistry relevance for it represents one of the first organic reactions whose mechanism was proposed by Arthur Lapworth. The mechanism is shown in scheme 1. The first step of the reaction is the nucleuphylic attack of the CN⁻ ion to the C=O of the benzaldehyde to form a cyanohydrin, subsequently the cyanohydrin attacks, in a nucleophilic manner, another benzaldehyde molecule to form the corresponding benzoin.

Reaction 1. Benzoin condensation reaction starting from benzaldehyde using KCN as catalyst.

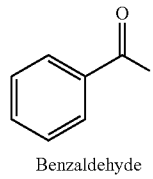

Benzaldehyde

Benzoin

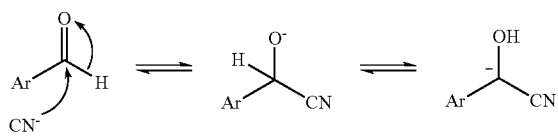

Scheme 1. Arthur Lapworth mechanism.

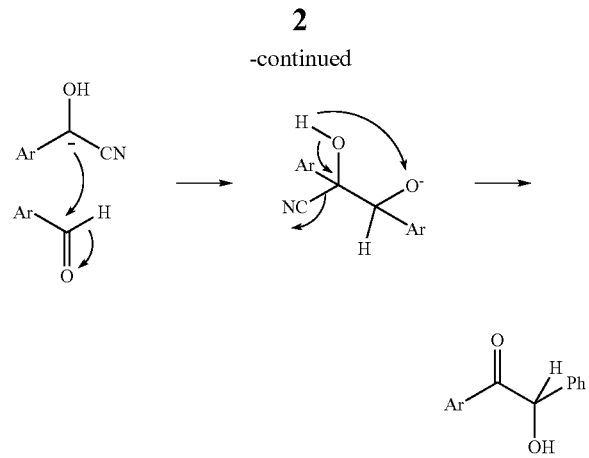

In the above reaction benzaldehyde is used as the starting chemical, while the dimerization of 2-pyridinecarboxalde-hyde in the presence of KCN produces very stable ethene-diols, (C. A. Buehler, Chem. Rev. 1964, 64, 7). From the dimerization of 2-pyridinecarboxaldehyde the product 1,2-di (2-pyridyl)ethene-1,2-diol results, this reaction was mistakenly referred to as the pyridoin condensation in resemblance to the benzoin reaction type shown below as Reaction 2. 1,2-Di(2-pyridyl)ethene-1,2-diol produces orange crystals when equal volumes of 2-pyridinecarboxaldehyde and glacial acetic acid or KCN are stirred together for several hours.

Reaction 2. Dimerization of 2-pyridinecarboxaldehyde using KCN as catalyst.

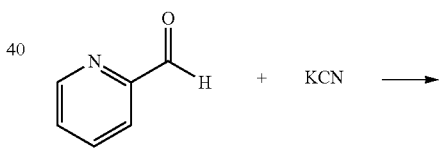

2-pyridinecarboxaldehyde

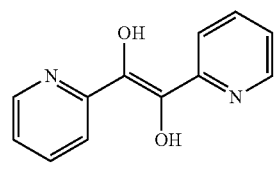

Alpha-pyridoin

The benzoin compound has the —COCHOH— group while the ethenediol compounds have the —(HO)C=C (OH)— group. Polymers with —(HO)C=C(OH)— parts have been prepared by polycondensation of pyridazine-2,3-dialdehyde, pyrazine-2,5-dialdehyde or from pyrimidine-4,6-dialdehyde catalyzed with KCN; the product obtained from these reactions is poly[di-1,2-(diazinilidene)ethene-1,2-diol], as shown in Reaction 3 below, (H. R. Wiley, U.S. Pat. No. 4,260,757).

Reaction 3. Polycondensation of pyrazine-2,5-dialdehyde, pyrimidine-4,6-dialdehyde and pyridazine-3,6-dialdehyde using KCN as catalyst.

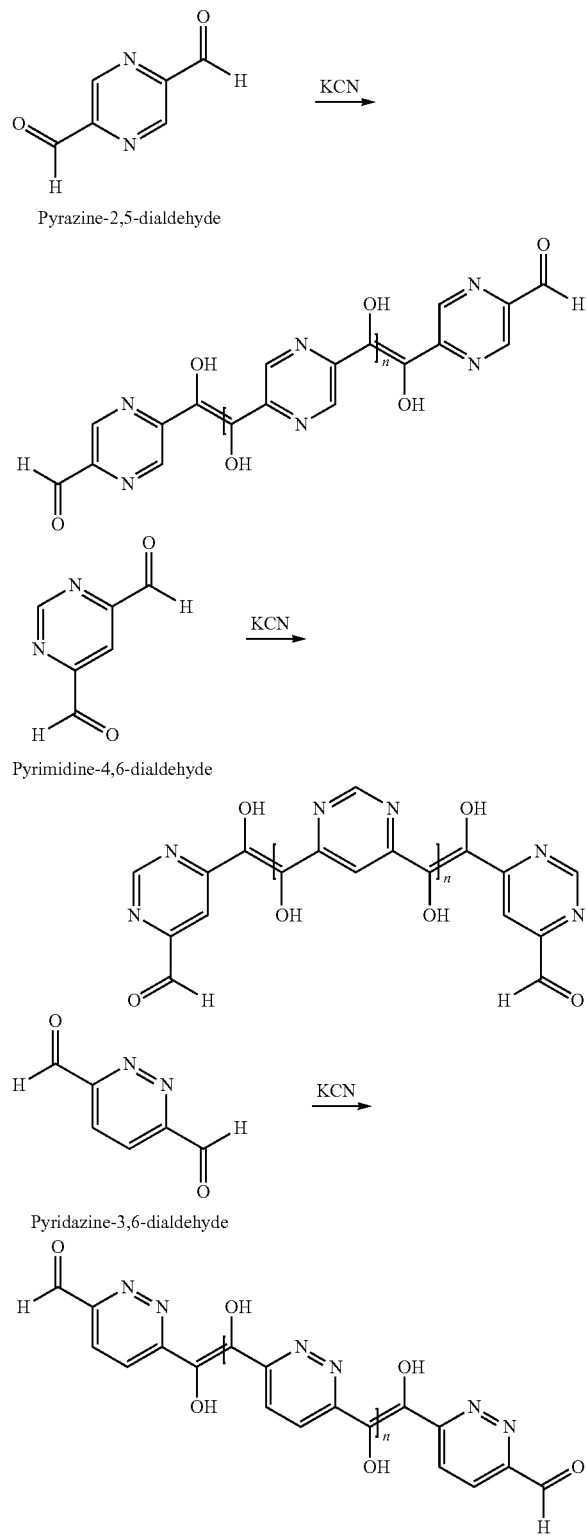

The drawbacks of the reported procedure to obtain ethenediols are that they are obtained from aromatic aldehydes which, as is well known in organic chemistry, are easily oxidized and therefore have to be previously subjected to purification procedures such as distillation so that they could be used for these type of reactions. The formation of the polymers shown in reaction 3 is from aromatic dialdehydes which are compounds sensitive to air because they are easily oxidized and difficult to obtain for the series of steps involved in the process, furthermore in some cases they are expensive ought to be made in situ to avoid oxidation prior to dimerization. Also, the catalyst (KCN) and solvents must be removed after each reaction to obtain pure products.

From the reaction at high temperature between 2-pyridinecarboxaldehyde and 2-pyridinemethanol, without catalyst and solvent, the product is 2-hydroxy-1,2-(2-pyridyl)-1-ethanone(2), which is deemed to be unstable in solution. Subsequently, compound (2) treated with solvents such as cyclohexane or ethyl acetate produces 1,2-di(pyridine-2-il)etheno-1,2-diol(1) or 1,2-di(pyridine-2-yl)ethane-1,2-dione(3)(2,2'-pyridyl) M. J. Percino, V. M. Chapela, S. Romero, C. Rodriguez-Barbarin, F. J. Melendez-Bustamante Journal of Chemical Crystallography, vol 36(5), 303, (2006) as shown in Reaction 4 that follows.

Reaction 4. Reaction between 2-pyridinecarboxaldehyde and 2-pyridinemethanol

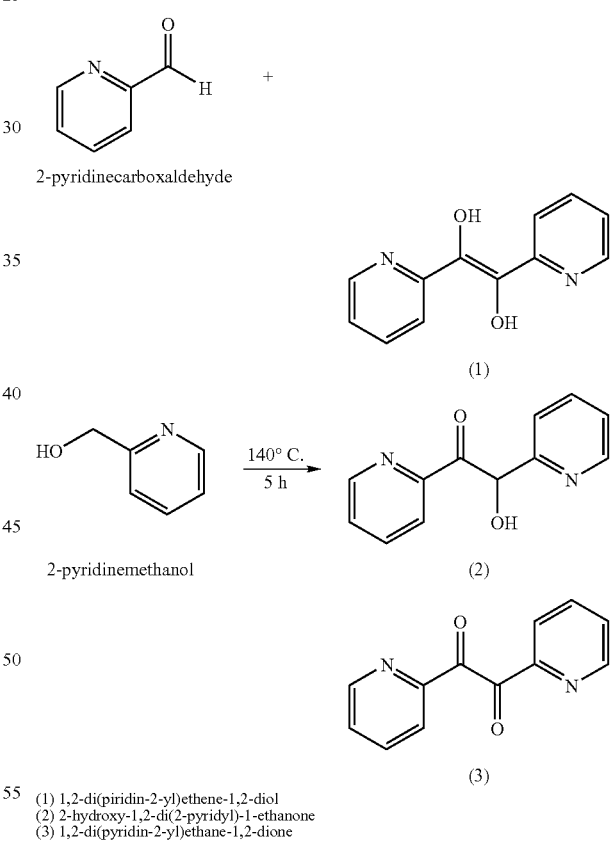

(1) 1,2-di(piridin-2-yl)ethene-1,2-diol
(2) 2-hydroxy-1,2-di(2-pyridyl)-1-ethanone
(3) 1,2-di(pyridin-2-yl)ethane-1,2-dione In addition, in the reaction between 2-pyridinecarboxaldehyde with (6-methylpyridine-2-yl)methanol shown below as reaction 5, the main products obtained are keto-enol compounds: 2-hydroxy-1,2-bis(6-methyl-2-pyridyl)-1-ethanone and 2-hydroxy-1-(6-methyl-2-pyridyl)-2-(2-pyridyl)-1-ethanone. Subsequent treatment with solvent produces 1,2-bis(6-methylpyridine-2-yl)ethane-1,2-dione and 1-(pyridine-2-yl)-2-(6-methylpyridine-2-yl)ethane-1,2-dione and in a much lesser quantity 1,2-bis(6-methylpyridine-2-yl)ethene-1,2- diol (M. J. Percino, V. M. Chapela, O. Urzua, H. Toribio, C. Rodriguez-Barbarin Journal of Chemical Research, (2007), 187).

Reaction 5. Reaction between 2-pyridinecarboxaldehyde and 6-methyl-2-pyridinemethanol.

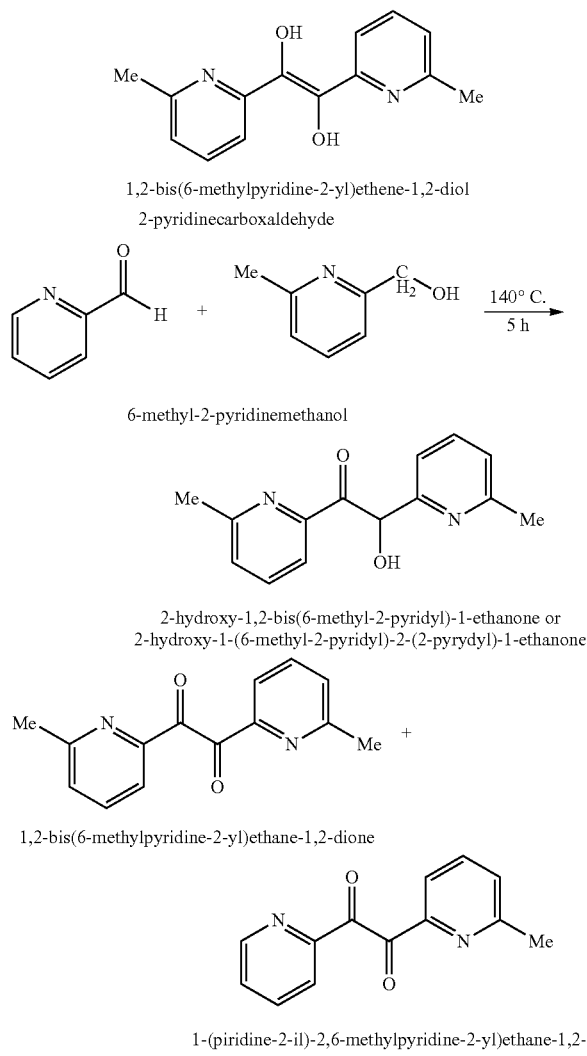

Reactions identified as 4 and 5, show several disadvantages due to the fact that from the reactions between aromatic aldehydes in the presence of different pyridinemethanol derivatives are produced products such as compound (2) reaction 4, and that by changing the solvent the expected corresponding low molecular weight ethenediols and α-diketones (3) are produced, aside other compounds that are also produced in some instances, this is, there is a mixture of products.

The process of the current invention, named Percino-Chapela has as one of its main novel features that starting from pyridinemethanol derivatives, the dimerization or coupling of pyridinic alcohols reaction is carried out avoiding oxidation as is the case when the starting materials are the corresponding aldehydes. It is a one step process to obtain compounds having the ethenediol group —(HO)—C=C—(OH). The products are orange or brown powders which may indicate a high electronic conjugation in their structure and are soluble in cyclohexane, methanol and DMSO.

The process of the current invention has as characteristic features the following: a) it is carried out in the absence or presence of some solvent, b) in the process of the current invention, the temperature may or may not be used as catalyst, c) in the process of the current invention the reaction may or may not be catalyzed by the presence of a catalyst (acid or base), d) the products may be obtained and separated in an easy way by precipitation, e) in the process of the current invention starting from pyridinic alcohols, ethenediols may be produced, in a single step reaction, f) pyridinemethanol derivatives used as starting chemicals do not oxidize as easily, their handling is not complex and their price is low, g) dimers, trimers, up to polymers compounds show high electronic conjugation or show charge transference that makes them colored compounds, stable at room temperature and atmospheric pressure, h) The products obtained through the process of the current invention, dimers, trimers, oligomers up to polymers are produced which are stable with outstanding properties that make them useful in the fields of electronics, optical and as inhibitors in polymerization and as antioxidants.

SUMMARY OF THE INVENTION

The present invention is directed to ethenediol products and a process to obtain ethenediols from pyridine derivative compounds. The various aspects of the invention are attained by providing a process for obtaining dimers, trimers, up to polymers from pyridinemethanol derived compounds, characterized in that it comprises reacting a compound of general formula (I) according to the following reaction:

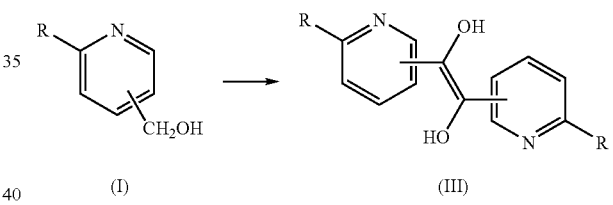

wherein R stands for H or —CH$_3$, in a coupling reaction, at a temperature of approximately 120 to 160° C., the reaction is catalyzed by temperature, the reaction time is approximately from 5 to 24 hrs., atmospheric pressure is used, the products are obtained by precipitation with a 2N NaOH solution, 2N HCl solution or H$_2$O, and correspond to a general formula (III), having an appearance of yellow-brown powders.

BRIEF DESCRIPTION OF THE DRAWINGS

The following is a brief description of the drawings, in which.

DETAILED DESCRIPTION OF THE PREFERRED EMBODIMENTS

Figure 1:
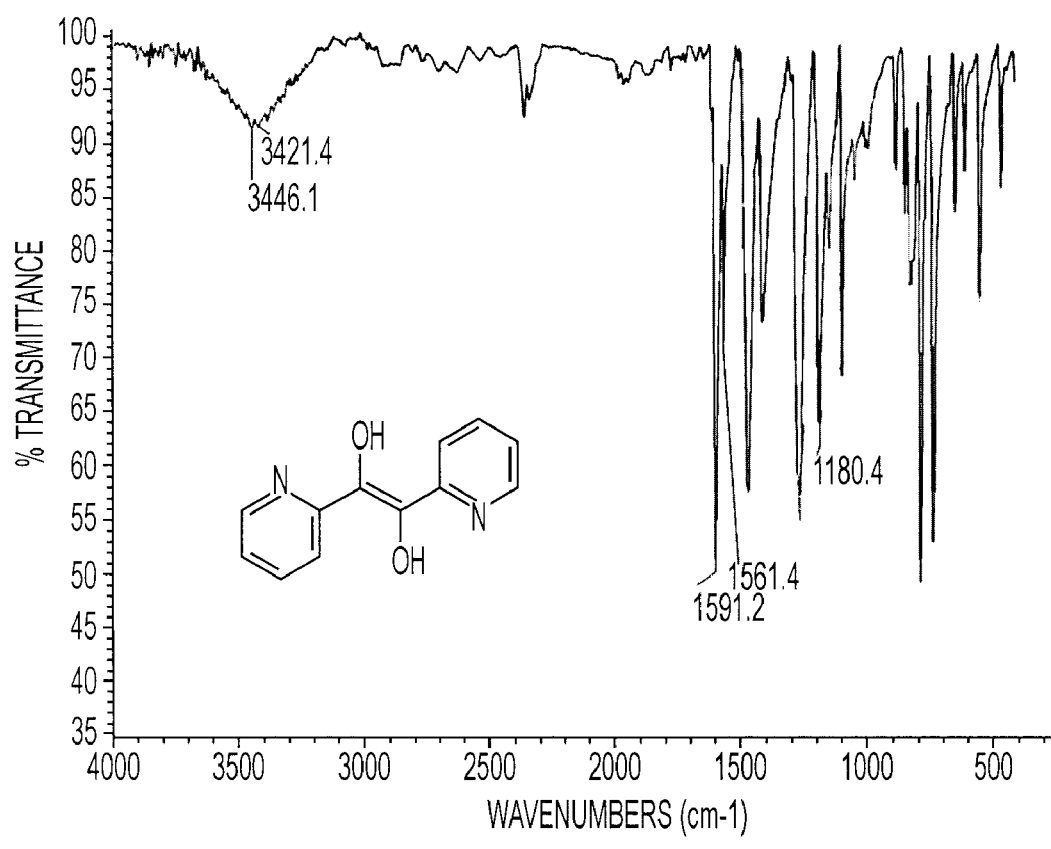
FIG. 1 is an IR spectrum of 1,2-di(2-pyridyl)ethene-1,2-diol.

As far as the knowledge of the applicant goes, there is no precedent about polymeric structures that contain in their structure parts such as —C(OH)=C(OH)—, —CO—CO— or —COH—CO— and that are produced from pyridinealcohols, as well as some known to date chemical process that discloses the dimerization or coupling of alcohols.

According to the current invention pyridinemethanol derivatives are used for the first time to react them to form compounds with repetitive structural entities of 1,2-(2-pyridyl)-etheno-1,2-diols.

The Percino-Chapela process of the current invention consists of a one step mass reaction. The reactions contemplated as of general character reactions that represent this process are shown in Reactions 6, 7 and 8. The process consists of the following stages: a) pyridinemethanol derivatives with general formula (I), wherein R represents H or $CH_3$, are made to react to get a product of the general formula (III), wherein R is H or $CH_3$; pyridinemethanol derivatives with a general formula (II), wherein R is $CH_3$ or —$CH_2$—OH, are made to react to get a product of the general formula (IV), wherein R is H or $CH_3$ and R' is H or —COH=COH—$C_5H_5N$, the reaction is carried out under reflux and without solvents for an approximate time between 5 and 24 hours at temperatures ranging from approximately 120 to 160° C., at atmospheric pressure; b) afterward the reaction mixture is precipitated by adding 1-3 N HCl solution, 1-3 N NaOH solution or water, to produce mainly powder of different colors.

Sometimes it is necessary to add a catalyst when the reaction is very slow or when the product yield is low after a long reaction time. A catalyst such as pyridine, triethylamine or similar base is made to react along with the reactant in a molar relationship between 0.5-1 relative to the reactant to react. The reaction is not an instantaneous one, starting from approximately 1:30 hrs. color changes start, mainly from yellow, red-orange, brown and darker. The products are brown and orange powders, soluble in cyclohexane, methanol, and DMSO, with melting point within the range of 100 to 250° C. Which may indicate a high electronic conjugation in the structure.

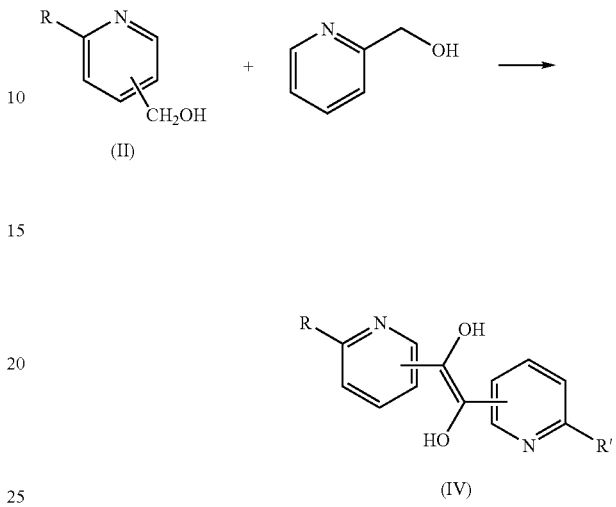

Reaction 7. General reaction to produce dimers, trimers, or oligomers of ethenediols.

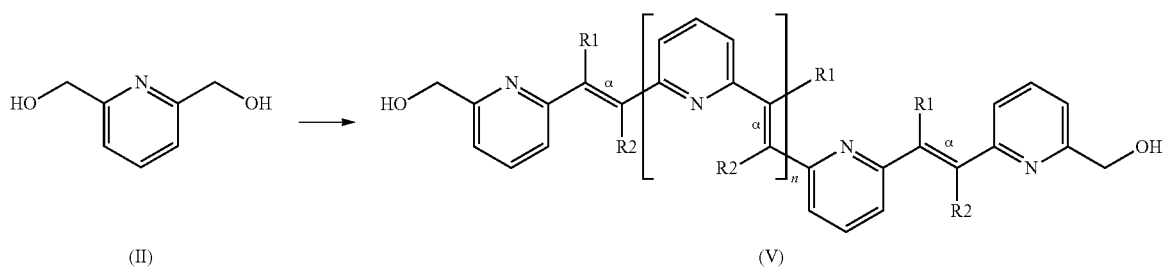

Reaction 8. General reaction to produce polymeric compounds from pyridinemethanols.

When in reaction 8 the general compound (II) has —$CH_2OH$ as equivalent for R and this is the only reactant in the reaction, the result are products with general formula (V) the meaning of $R_1$ being —OH or =O and $R_2$ being —OH or =O, $R_1$ and $R_2$ being the same or different, when $R_1$ or $R_2$ is =O the α bond is a single bond.

In order to illustrate the process of the current invention, the following examples of the uses of the invention are described below.

EXAMPLES

Example 1

Figure 2:
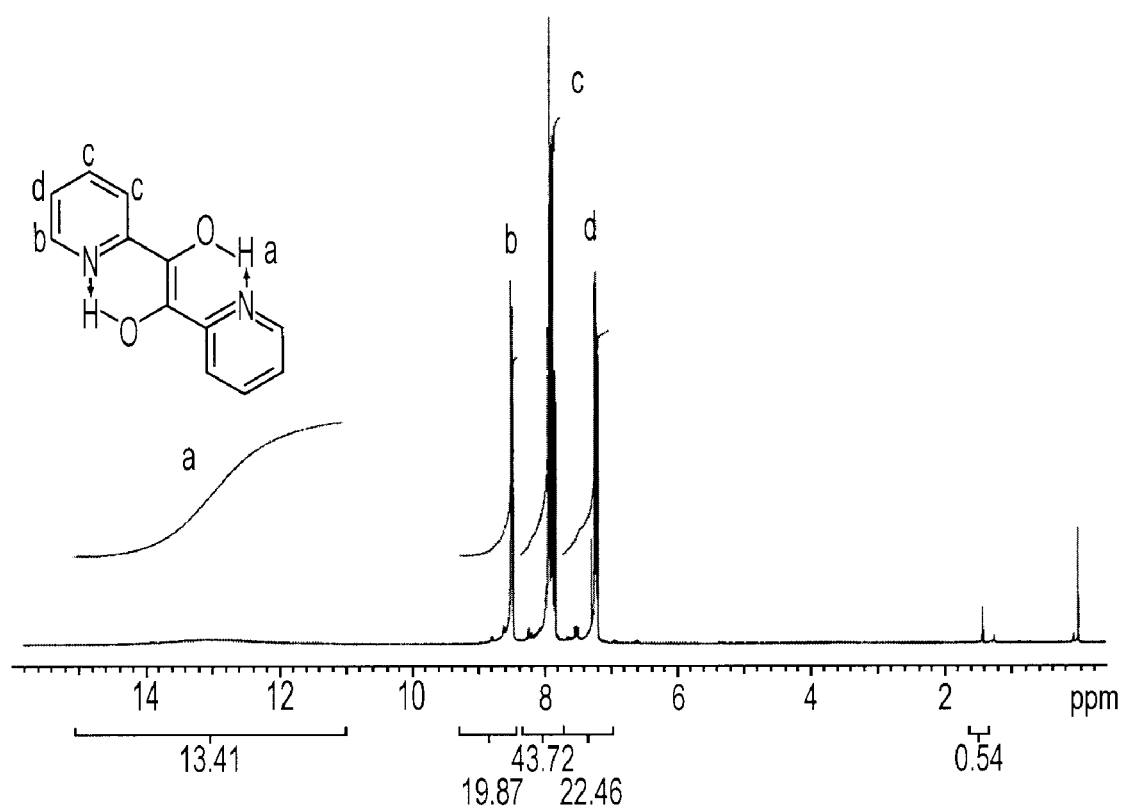
FIG. 2 is an NMR spectrum of 1,2-di(2-pyridyl)ethene-1, 2-diol.

The current example refers to general reaction 6; it is carried out as a coupling reaction using as starting chemicalinitial 2-pyridinemethanol recently distilled, the reaction is catalyzed with temperature, the values of which are approximately 153 to 155° C. It is carried out under atmospheric pressure, for approximately 24 hours, pyridine is added as a catalyst in a molar ratio 1:1. The products corresponding to general formula (III) are obtained through precipitation with a solution of 2N NaOH, 2N HCl or $H_2O$, they have got a yellow-brown powder appearance, which were characterized Reaction 6. General reaction to produce low molecular weight ethenediol compounds.

through the analytical techniques known as IR Infrared, Nuclear Magnetic Resonance NMR'H and mass spectrometry, in FIG. 1 the IR spectrum is shown, and in FIG. 2 that of the NMR. The evidence through IR which indicated the presence of the 1,2-di(2-pyridyl)-1,2-ethenediol in Example 1 (FIG. 1) was the band at 3448 to 3421 cm$^{-1}$ assigned to the vO—H vibration, the band at 1180 cm$^{-1}$ assigned to the vC—O vibration of alcohol, and the band at 1590 cm$^{-1}$ assigned to the vC=N vibration of the pyridinic ring.

In FIG. 2, the NMR proton spectrum for the 1,2-di(2-pyridyl) 1,2-ethenediol. The molecule is symmetrical and therefore the signals that indicated its formation were a wide signal at 12.923 ppm assigned to the OH proton (a) with an integration of 2H, the multiplet between 8.479-8.453 ppm corresponds to the two protons in position 6 of the pyridinic ring (b), the multiplet between 7.930-7.808 ppm can be assigned to four protons of both rings; two protons one in position 4 and two in position 3 of the ring (c). Lastly, the multiple signals between 7.21-7.166 ppm was assigned to the two protons in position 5 of the pryridinic ring (d).

Figure 3:
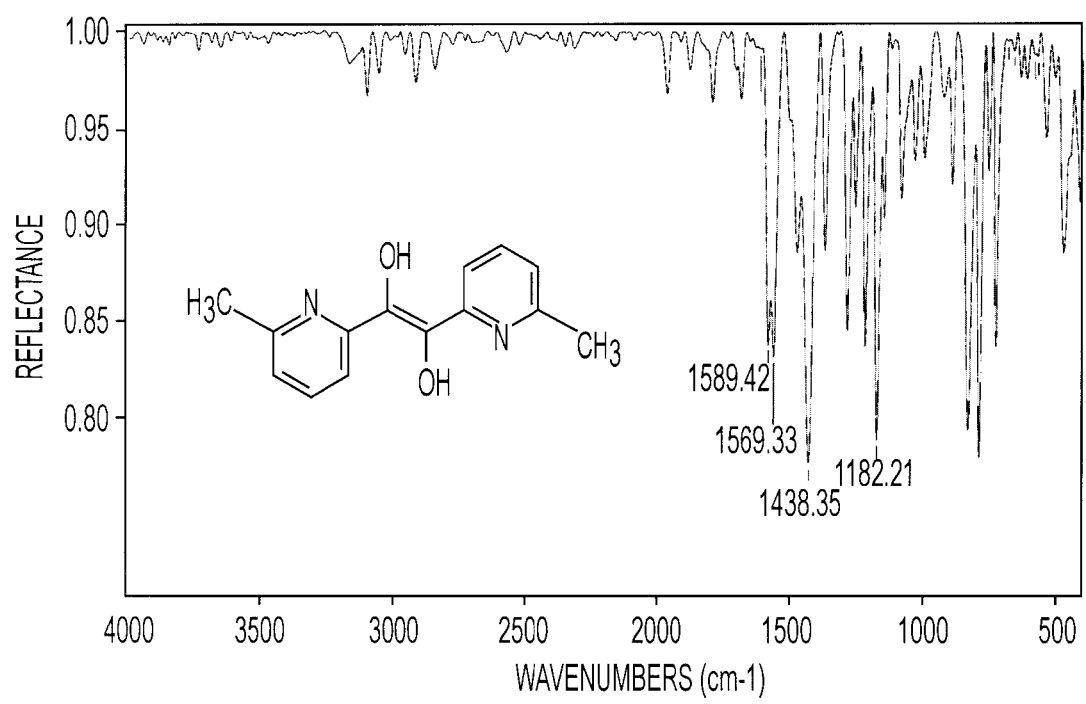
FIG. 3 is an IR spectrum of 1,2-bis(6-methylpyridine-2-yl) ethene-1,2-diol.
Figure 4:
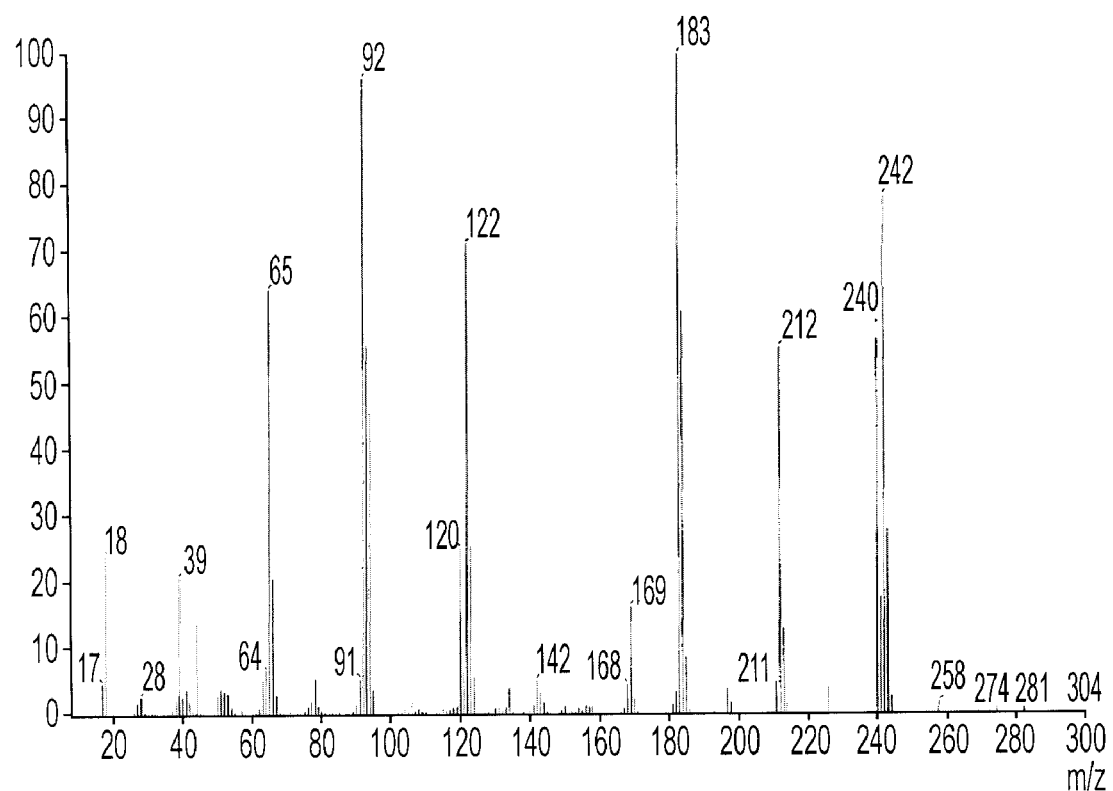
FIG. 4 is an electronic impact spectrum of 1,2-bis(6-methylpyridine-2-yl)ethene-1,2-diol.

The evidence from IR FIG. 3, which indicated the presence of 1,2-bis(6-methylpyridine-2-yl)ethene-1,2-diol was the band at 1226 cm$^{-1}$ assigned to the vC—O vibration of alcohol and the band at 1180 cm$^{-1}$ owing to the deformation vibration of the O—H. The bands at 1590 and 1569 cm$^{-1}$ assigned to the vC=N and C=C vibration of the pryridinic ring. The band a 3448-3421 cm$^{-1}$ assigned to the vO—H vibration. The mass spectrum FIG. 4, gave the molecular ion 242 m/z (M+), which corresponds to the theoretical molecular weight of 242 g/Mol for the 1,2-bis[2-(6-methylpyridine-1-yl)ethene-1,2-diol].

The products obtained when the meaning of R is hydrogen are: 1,2-di(pyridine-2-yl)ethene-1,2-diol and 1,2-di(pyridine-4-yl)ethene-1,2-diol.

Example 2

The Example refers to general reaction 7; to obtain oligomers, the molar relation used is 1:1 of 6-methyl-2-pyridinemethanol to 2-pyridinemethanol, the reaction is carried out at a temperature of approximately 140° C., at atmospheric pressure, for approximately 24 hours. The product is obtained when the solution is precipitated with 2 N NaOH, the product obtained corresponds to the general formula (IV), and it has a molecular weight in the interval of 228 g/mol. The product is an orange or brown powder, soluble in CHCl$_3$, C$_6$H$_{12}$, cyclohexane and THF, with a melting point of 128-133° C.

The product preferably obtained is [1-(6-methylpyridine-2-yl)-2-(pyridine-2'-yl)]ethene-1,2-diol.

Example 3

Similar to Example 2, a reaction is carried out where the reactants molar ratio is 1:2 of 2,6-pyridinedimethanol with 2-pyridinemethanol. The reaction conditions used were: a temperature of approximately 140° C., at atmospheric pressure for about 24 hours, the resulting product corresponds to general formula (IV), and has a molecular weight of 243 or 333 g/mol depending on whether it is of two or three rings with terminal groups —CH$_2$OH. The products are dark brown powders soluble in CH$_3$OH and DMSO, with melting point of 200-250° C.

The product preferably obtained is 2,6-di[(pyridine-2'-yl)ethene-1,2-diol] —COH=COH—NC$_5$H$_5$ Example 4

This is similar to Examples 1 and 2, the example specifically refers to general reaction 8, which is carried out using pyrindinedimethanols to obtain polymers such as: poly[2-hydroxy-(1,2-di(pyridine-2-yl)ethane-1-one], poly[1,2-di(pyridine-2-yl)ethane-1,2-dione] and poly[1,2-di(pyridine-2-yl)ethene-1,2-diol] with grade of polymerization n in an interval of 10-30 monomeric units, these are obtained as a brown soluble powder in DMSO with melting point between 161-164° C., by precipitation with 2N HCl solution, after a reaction time of 24 hours, reaction temperature of 140° C. at atmospheric pressure. The molecular weight is approximately between 2182-6422 g/mol.

The products obtained with ethenediol parts can be applied as antioxidants due to their capacity as free radical inhibitors.

What is claimed is:

1. A process for producing ethendiol derivatives by reacting 2,6-pyridinedimethanol and 2-pyridinemethanol as the only reactants, wherein the molar ratio of the reagents is 1:2 of 2,6-pyridinedimethanol to 2-pyridinemethanol, the reaction temperature is of approximately 120 to 160° C., the reaction time is approximately 5 to 24 hrs, and the resultant product is 2,6-di[1-(pyridine-2'-yl)-1,2-dihydroxy(ethene)]pyridine with a molecular weight of 349 g/mol.

2. The process of claim 1, wherein the reaction temperature is approximately 140° C. and the reaction time is approximately 24 hours.

3. A process for producing polymers from pyridinemethanol and derivatives thereof according to the following reaction:

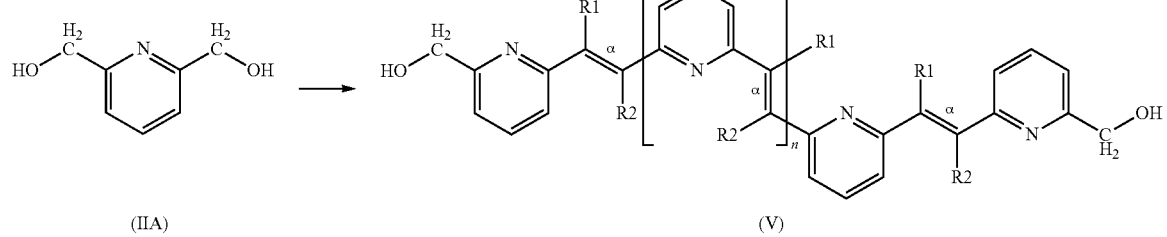

(IIA)      (V)

wherein R$_1$ is —OH or =O and R$_2$ is —OH or =O, wherein R$_1$ and R$_2$ are either the same or different, when R$_1$ or R$_2$ is =O, the α bond is a single bond, the resultant products are a brown powder soluble in DMSO with melting point between 161-164° C. produced by precipitation with an 2N HCl solution, after a 24 hr reaction time, reaction temperature of 140° C. at atmospheric pressure, the compounds are produced where n is 10-30 with a molecular weight of approximately 2182-6422 g/mol.

4. The process for producing polymers from pyridinemethanol derivative compounds according to claim 3, wherein the resultant products are selected from the group consisting of Poly[2-hydroxy-(1,2-di(pyridine-2-yl)ethane-1-one]; poly[1,2-di(pyridine-2-yl)ethane-1,2-dione] and poly[1,2-di(pyridine-2-yl)ethene-1,2-diol] where n is 10-30.

5. The process of claim 3, wherein the process comprises reacting a reaction mixture where the compound IIA is the only reactant.

* * * * *

UNITED STATES PATENT AND TRADEMARK OFFICE
CERTIFICATE OF CORRECTION

| | | |
|---|---|---|
| PATENT NO. | : 7,989,583 B2 | Page 1 of 1 |
| APPLICATION NO. | : 12/183167 | |
| DATED | : August 2, 2011 | |
| INVENTOR(S) | : Maria Judith Percino Zacarias et al. | |

It is certified that error appears in the above-identified patent and that said Letters Patent is hereby corrected as shown below:

On the cover page item (73), add the following two assignees:

Maria Judith Percino Zacarias, Puebla, MX; and

Victor Manuel Chapela Castanares, Puebla, MX.

Signed and Sealed this
First Day of November, 2011

David J. Kappos
*Director of the United States Patent and Trademark Office*